(12) United States Patent
Cole (10) Patent No.: US 7,075,646 B2
(45) Date of Patent: Jul. 11, 2006

(54) SMOKE DETECTORS PARTICULARLY DUCTED SMOKE DETECTORS

(76) Inventor: Martin Terence Cole, 36 Acacia Court, Patterson Lakes, Victoria (AU) 3197

( * ) Notice: Subject to any disclaimer, the term of this patent is extended or adjusted under 35 U.S.C. 154(b) by 162 days.

(21) Appl. No.: 10/203,454

(22) PCT Filed: Feb. 9, 2001

(86) PCT No.: PCT/AU01/00121

§ 371 (c)(1),
(2), (4) Date: Aug. 9, 2002

(87) PCT Pub. No.: WO01/59737

PCT Pub. Date: Aug. 16, 2001

(65) Prior Publication Data

US 2003/0011770 A1   Jan. 16, 2003

(30) Foreign Application Priority Data

Feb. 10, 2000 (AU) ................................ PQ5538

(51) Int. Cl.
*G01N 21/00* (2006.01)
*G01J 4/00* (2006.01)
(52) U.S. Cl. .................... 356/338; 356/364
(58) Field of Classification Search ........ 356/432–440, 356/335–343, 364–370; 340/630, 693; 250/573, 250/574, 579
See application file for complete search history.

(56) References Cited

U.S. PATENT DOCUMENTS

| | | | |
|---|---|---|---|
| 3,616,410 A | 10/1971 | Shtoffer | 204/195 |
| 3,982,130 A | 9/1976 | Trumble | |
| 4,288,790 A * | 9/1981 | Schnell | 340/628 |
| 4,379,290 A * | 4/1983 | Muggli et al. | 340/629 |
| 4,426,640 A | 1/1984 | Becconsall et al. | 340/632 |
| 4,906,978 A | 3/1990 | Best et al. | |
| 5,372,477 A | 12/1994 | Cole | 415/218.1 |
| 5,440,145 A | 8/1995 | Cole | 250/574 |
| 5,502,434 A * | 3/1996 | Minowa et al. | 340/630 |
| 5,576,697 A * | 11/1996 | Nagashima et al. | 340/630 |
| 5,665,925 A | 9/1997 | Gerteis | 73/865 |
| 5,755,250 A | 5/1998 | Cole | 137/78.5 |

(Continued)

FOREIGN PATENT DOCUMENTS

AU           573243           6/1988

(Continued)

OTHER PUBLICATIONS

D. S. Goodman, "Method for Localizing Light-Scattered Particles," IBM Technical Disclosure Bulletin, vol. 27, No. 5, Oct. 1984, pp. 3164.

*Primary Examiner*—Michael P. Stafira
(74) *Attorney, Agent, or Firm*—Kusner & Jaffe (57) ABSTRACT

The present invention relates to the detection of particles suspended in fluid particularly smoke detectors suitable for mounting on ducting for the early detection of smoke created by unwanted pyrolysis or combustion of materials in a protected area or fire zone to which the duct is connected. The present invention provides alternately illuminating a detection zone with one of either a first or a second illumination. The improvement embodied in the current invention is the ability to retain sensitivity to a wide range of particle sizes and also to discriminate between different kinds of smoke or dust according to particle size, whilst also achieving relatively long service life, small size, light weight and low cost.

22 Claims, 6 Drawing Sheets

U.S. PATENT DOCUMENTS

| | | | |
|---|---|---|---|
| 5,841,534 A | 11/1998 | Lorenz | 356/336 |
| 6,184,537 B1 | 2/2001 | Knox et al. | 250/574 |
| 2002/0101345 A1 | 8/2002 | Pattok et al. | 340/516 |

FOREIGN PATENT DOCUMENTS

| | | |
|---|---|---|
| AU | 573594 | 6/1988 |
| AU | 575845 | 8/1988 |
| AU | 576361 | 8/1988 |
| AU | 577538 | 9/1988 |
| AU | 577551 | 9/1988 |
| AU | 80708/91 | 1/1992 |
| AU | 27746/92 | 5/1993 |
| AU | 40503/93 | 12/1993 |
| AU | 40504/93 | 12/1993 |
| AU | 663758 | 10/1995 |
| EP | 0 076 338 | 4/1983 |
| EP | 463795 A | 6/1990 |
| EP | 0 463 795 | 1/1992 |
| GB | 1 527 965 | 10/1978 |
| GB | 2 193 570 | 2/1988 |
| GB | 2 267 963 | 12/1993 |
| GB | 2267963 A | 12/1993 |
| GB | 2 273 769 | 6/1994 |
| GB | 2273769 A | 6/1994 |
| GB | 2 319 604 | 5/1998 |
| GB | 2 319 605 | 5/1998 |
| GB | 2319604 A | 5/1998 |
| GB | 2319605 A | 5/1998 |
| WO | WO 00/07161 | 2/2000 |
| WO | WO 00/07161 A | 2/2000 |

\* cited by examiner

Fig 2.
Section 2-2

Fig 1a.
Section 1-1

Fig 4.
Section 4-4

Fig 3.
Section 3-3

SMOKE DETECTORS PARTICULARLY DUCTED SMOKE DETECTORS

CROSS REFERENCE TO RELATED APPLICATIONS

This is a U.S. National Phase Application under 35 U.S.C. § 371 of International Application No. PCT/AU01/00121 filed Feb. 9, 2001, which was published Under PCT Article 21(2) in English, which claims priority to Australian Application No. PQ 5538, filed Feb. 10, 2000, the entire contents of which are incorporated herein by reference.

FIELD OF INVENTION

The present invention relates to the detection of particles suspended in fluid particularly smoke detectors. The invention is suitable for mounting on ducting for the early detection of smoke created by unwanted pyrolysis or combustion of materials in a protected area or fire zone to which the duct is connected.

The ducting may be ventilation or air-conditioning ducting used in controlling the temperature and/or quality of air in the protected area.

The invention, equally may be free standing or provided in an open environment, that is, the invention does not require duct mounting. The examples disclosed are provided by way of explanation of the invention, only, and duct mounting is merely one preferred embodiment. The scope of the invention should not be so limited.

Duct mounted smoke detectors take a small sample of air passing through an air duct such as a ventilator shaft and are intended to detect the presence of smoke in the sample and thereby raise an alarm if the concentration of smoke exceeds a predetermined value indicative of the presence of a fire in the protected area.

Presently, conventional point type smoke detectors, primarily designed for ceiling installation in a protected area, are used for ducted mounting. The detector is mounted inside a sealed housing to be mounted external to a duct, the housing is fitted with a pair of straight tubular probes which are fitted inside the duct and adapted to draw a continuous small sample of air from the duct interior and to pass the sample or part thereof through the adjacent detector.

Difficulties arise if the smoke is significantly diluted as a result of large volumes of air passing through the duct. Faced with this dilution, it has been found that such detectors have insufficient sensitivity to provide a warning that is appropriately early for life safety. Moreover, although a bug screen and dust filter is often included to protect the detector from soiling, this is generally inadequate to prevent clogging of passages or soiling of optical surfaces. Such detectors are inherently unreliable due to moisture condensation, soiling and false alarms caused by dust, and are generally acknowledged to have an unsatisfactory service life measured only in months.

To overcome these disadvantages, high-sensitivity aspirated smoke detectors have been employed for duct monitoring. These detectors provide a sensitivity some hundreds of times greater than conventional, point detectors, thereby overcoming the smoke dilution.

The suction pressure available from the aspirator (air pump) can overcome the restriction of the dust filter, enabling a more efficient filter to be employed thereby avoiding unwanted dust pollution and possible false alarms.

Aspirated smoke detection has already been improved over many years by the inventor as described in his Australian patent numbers 575845, 3184384, 4229885, 3023684, 3184184, 3453784, 3400593, 8070891, 2774692, 4050493 and 4050393, with corresponding patents overseas including Western Europe, North America, Japan and New Zealand.

An aspirated smoke detector employs an aspirator to draw a continuous sample of air through a dust filter and the smoke detection chamber. This aspirator may also draw samples of smoke from a ventilation duct, or alternatively through pipework for long distances.

In the case of pipework, this is of small bore and is often mounted on a ceiling with sampling holes drilled at regular intervals, enabling samples of air to be actively drawn from throughout the protected area. By contrast, conventional types of smoke detector rely upon convection currents or air draughts to passively draw the smoke through the detector chamber.

Whether intended for a duct or pipework application, ideally the smoke detector employed within an aspirated smoke detection system is a nephelometer. This is a detector that is sensitive to all sizes of smoke particles produced in fires, or during the early stages of overheating, pyrolysis or smoldering (which usually occurs for at least an hour prior to the appearance of flame).

Optical type smoke (or airborne particle) detectors of the prior art typically use a single light source (or projector) to illuminate a detection zone that may contain such particles. A proportion of this light may be scattered off the particles towards a single receiver cell (or sensor) that is positioned to provide acceptable detection performance. Improved versions of the prior art include one or more additional sensors positioned to receive light scattered in different direction(s). The output signals from these two or more sensors are utilized for the purpose of providing further information about the particle size, or the average size of a group of particles. A disadvantage of this prior art is that it uses a source of light having a single wavelength, and is insensitive to the small particles produced in flaming fires.

Other detection techniques use a laser beam, providing a polarized monochromatic light source, typically in the near infrared wavelength. Such detectors are prone to having a high sensitivity to large particles, at the expense of having low sensitivity to small particles (that is, smaller than the wavelength of light). Thus a laser-based detector does not operate as a true nephelometer. This disadvantage can be reduced by the use of a plurality of receiving sensors positioned to detect light scattered at various angles and polarizations, but only one light wavelength is used.

Some aspirated smoke detectors have used a single laser diode beam but this suffers the same disadvantage of using a single wavelength and has low sensitivity to smoke from flaming fires. Other disadvantages of using aspirated detectors lie in terms of high cost, energy consumption, complexity and size.

The disadvantage exhibited by all of the above prior art whether aspirated or not, namely their insensitivity to small particles characteristic of flaming fires, has in many instances demanded the installation of additional ionization type smoke detectors. These detectors utilize a radioactive element such as Americium, to ionize the air within a chamber. The conductivity of this chamber is reduced when smoke particles displace ionized air, causing an alarm to be operated. Such detectors are sensitive to the small particles produced in flaming fires but are insensitive to the large particles produced in pyrolysis or smoldering. These detectors are also prone to false alarms caused by draughts which similarly displace ionized air. Accordingly the insensitivity to incipient fires and the propensity toward false alarms renders ionization type detectors an unacceptable alternative.

Other, aspirated smoke detectors have used a Xenon lamp as the single light source that produces a continuous light spectrum similar to sunlight, embracing ultraviolet, visible and infrared wavelengths. Use of this continuous spectrum can detect particles of all sizes and produce a signal that is proportional to the mass density of smoke, which is hitherto the most reliable measure of fire development. Although this can function as a true nephelometer, it does not characterize the type of fire. A disadvantage is the inability to select particular wavelengths unless a complex, costly and comparatively unreliable system of mechanically moving color filters is used. Further disadvantages of this technique are the service life of the Xenon lamp which is typically limited to 4 years, the variation in light intensity and the costly high voltage power supply required.

Other prior art has used two light sources. GB 2193570 by Kane & Ludlow (May 10, 1980), for example, describes the use of one laser beam to detect the size and sphericity of airborne particles, requiring no less than five accurately positioned sensors. A second laser beam of the same wavelength is used to gate on and off the first laser, according to the presence of a single particle in the field of view.

This second laser is used to improve the signal-to-noise ratio of the system, but not to determine the particle size or sphericity. Such a system is too costly for the high-volume fire alarms industry.

As another example, U.S. Pat. No. 4,426,640 by Beconsall et al. (May 8, 1986) describes a pollutant gas detector using two light sources but this is not an airborne particle counter. This uses a first laser operating at the absorption wavelength of the gas to be detected, and a second laser operating at a reference wavelength which is necessarily similar, but not identical to the absorption wavelength. The two laser beams are projected to "infinity" through the atmosphere (surrounding a chemical plant) and the relative intensity of the signals received at each wavelength provides a measure of the concentration of the pollutant gas.

It would be understood that the type of smoke produced in various pyrolysis and combustion circumstances is different. Fast flaming fires tend to produce a very large number of very small solid particles which may agglomerate into random shapes to form soot. In contrast, the early stages of pyrolysis tend to produce a much smaller number of quite large liquid particles (of high boiling point), typically existing as aerosols that may agglomerate to form larger, translucent spheres.

It has been found that the detection of large particles which slowly increase in quantity over an extended period of time would indicate a pyrolysis or smoldering condition, requiring some attention.

Alternatively, the detection of numerous small particles arising quickly and without an earlier pyrolysis or smoldering period, would tend to indicate arson where accelerants have been used and the need for immediate action. An ability to distinguish between these extremes would assist the building operator, fire brigade or automatic fire alarm system in determining the appropriate response to the threat.

Another aspect of the prior art is its susceptibility to dust. Dust is important in two ways. Firstly, airborne dust is generally interpreted by the detector as smoke, so elevated dust levels can cause false fire alarms. Secondly, even if discrimination means was used to reduce the rate of false alarms, there remains the problem of soiling. Soiling is the slow build-up of dust within the detector. This can affect the reliability of the detector by reducing its sensitivity to smoke and/or by reducing its safety margin against false alarms. The service life of a detector is principally governed by soiling which consequently requires regular maintenance. A detector that can minimize soiling and can discriminate against smoke particles would be of advantage. Moreover, in certain applications the ability to identify the presence of dust could be used to monitor the cleanliness of an area. This particular role has hitherto required the use of very expensive dust particle counters as used in the microchip fabrication industry which are highly prone to soiling when applied to office type environments.

A smoke and/or dust detector that is rugged, of small size and of lightweight would be an advantage for applications in the aerospace industry.

OBJECTIVE OF THE INVENTION

It is an objective of the present invention to provide a smoke detector device having the ability to detect a wide range of particle sizes and to discriminate between different kinds of smoke or dust according to particle size. The smoke detector device is suitable for mounting onto an air conduit or ventilation duct. It is an objective to provide a smoke detector and a detection system having a relatively long service life with relatively long intervals between servicing.

It is an objective to provide a smoke detection system of relatively high sensitivity capable of use without an aspirator.

STATEMENT OF INVENTION

There is provided according to a first aspect of the present invention a device for the detection of particles suspended in a fluid, the device including light source(s) adapted to provide at least a first polarized illumination and a second polarized illumination, a particle detection zone through which a stream of sample fluid is adapted to flow, logic means adapted to alternately illuminate the detection zone with either the first or second illumination, sensor means for reception of light scattered off particles within the detection zone and output means to provide an indication of a predetermined condition in the detection zone.

Preferably, at least one of the polarized first and second illumination is provided by light from the light source(s) being projected through polarizing filters, each with a different relative polarization.

Preferably, at least one of the polarized first and second illumination is provided by a source of light having different polarization.

Preferably, the source of light having different polarization is a laser diodes set to different polarization and/or wavelength.

Preferably, the above device has light source(s) which include at least 2 light sources, the components of the device are mechanically fixed in position, the first and second illuminations are independently radiated, the first and second illuminations are of different polarization, the first and second illuminations are provided from different positions, and/or the first and second illuminations are of different wavelength such as one of short wavelength light and the other of long wavelength light.

There is provided according to a second aspect of the present invention a device for the detection of particles suspended in a fluid, the device including a body portion, light source(s) adapted to provide at least a first illumination and a second illumination, a particle detection zone through which a stream of sample fluid is adapted to flow, logic means adapted to alternately illuminate the detection zone with either the first or second illumination, sensor means for reception of light scattered off particles within the detection zone and output means to provide an indication of a predetermined condition in the detection zone, wherein the body portion is configured from two substantially similar halves.

Preferably, the first and second illuminations are disposed substantially opposite an area of particle detection.

Preferably, the body portion is configured substantially axially similar.

The above device(s) may or may not be duct mounted.

Preferably, the light source(s) includes a pair of light sources, one of short wavelength light the other of long wavelength light.

The improvement embodied in the current invention is the ability to retain sensitivity to a wide range of particle sizes and also to discriminate between different kinds of smoke or dust according to particle size, whilst also achieving relatively long service life, small size, light weight and low cost.

The light source(s) may be adapted to project light at the same angle relative to the detection zone axis, or, alternatively, at a different angle.

Typically the light source(s) is operated in a pulse mode such that only one wavelength is operated at one time. The system gain within the electronic circuitry is adjusted so that under calibration conditions, each light source can produce the same signal level at the receiving sensor. In addition the receiving sensor is selected for its suitable bandwidth of operation (sensitivity to all of the wavelengths employed).

More than two wavelengths of light or polarized light or a combination of the two may be utilized to achieve very high sensitivity to, or discrimination of, various types of particles encountered in the detection chamber whether they be small or large smoke particles or dust particles.

The receiving sensor may also have a polarizing filter. Operating none, or all of the light source(s) together at one time is also possible.

Thus, the light source(s) may be pulsed in sequence and both the absolute and relative amplitude of pulses received at the sensor are analyzed to determine the smoke concentration and the particle size distribution, thereby to characterize the smoke type.

According to a third aspect of the invention, there is provided a smoke detector and smoke detection method, in which the detector has a body, at least two light projectors mounted within the body for projecting light into a detection zone adapted to receive an air sample, at least one light receiving sensor mounted in the body to receive scattered light from the zone, the arrangement being such that the projected light in pulses of differing wavelength, polarization and/or angle impinging upon the smoke and dust particles entering the detection zone will create scattered light indicative of a range of smoke particle sizes and/or the existence of dust particles, said sensor upon receiving at least some of said scattered light being adapted to provide a signal which upon analysis enables the determination of smoke concentration and particle size and/or size range.

According to a fourth aspect of the present invention, there is provided a method of smoke detection and a particle, smoke or dust detector including a body having an inlet through which sample(s) of fluid, including air, can be provided, and output means for indicating an alarm condition, the method and detector using a particle detection unit having a source of light, and a particle size discrimination means, wherein the alarm condition is provided by analyzing over a predetermined period of time a change in the concentration of selected particle size(s) and/or range(s).

Preferably, the particle size(s) and/or particle range(s) determined are relatively large particle size(s) and/or range(s).

Preferably, an alarm condition indicative of pyrolysis is provided upon determining a relatively slow increase in large particle size(s) and/or range(s).

Preferably, the particle size(s) and/or range(s) determined are relatively small particle size(s) and/or range(s).

Preferably, an alarm condition indicative of a flaming fire is provided upon determining a relatively rapid increase in small particle size(s) and/or range(s).

Preferably, an alarm condition indicative of an accelerant being used is provided upon determining that prior to the rapid increase in small particle size(s) and/or range(s), there was a small, if any, period of pyrolysis.

Preferably, airborne dust content is determined in order to reduce false alarms.

Preferably, separate alarm output is provided for any one of, or any combination of, the alarm conditions noted above.

Preferably, the particle size discrimination means includes a first light source for detecting relatively small particle size(s) and/or range(s) and a second light source for detecting relatively large particle size(s) and/or range(s).

Preferably, the first and second light source are alternatively active.

Preferably, the particle size discrimination unit utilizes a relatively short wavelength of light and a relatively long wavelength of light to detect particle size and/or range.

A still further aspect is directed to a smoke detector including the detection unit and/or operatively adapted to detect an alarm condition as disclosed herein.

A fifth aspect of the present invention provides an alarm detector and method of detecting an alarm condition for a pyrolysis, smoldering and/or smoke event, where a sample of fluid is provided, upon the fluid sample, impinging light emanating from a source of light, from the emanating light determining particle size(s), and over a predetermined period of time, determining whether the number or concentration of selected particle size(s) and/or range(s) has changed, in consequence of which an alarm can be provided if the determination of concentration of number of particles of selected particle size(s) and/or range(s) falls within selected criteria.

Preferably, the particle size(s) and/or particle range(s) determined are relatively large particle size(s) and/or range(s).

Preferably, an alarm condition indicative of pyrolysis is provided upon determining a relatively slow increase in large particle size(s) and/or range(s).

Preferably, the particle size(s) and/or range(s) determined are relatively small particle size(s) and/or range(s).

Preferably, an alarm condition indicative of a flaming fire is provided upon determining a relatively rapid increase in small particle size(s) and/or range(s).

Preferably, an alarm condition indicative of an accelerant being used is provided upon determining that prior to the rapid increase in small particle size(s) and/or range(s), there was a small, if any, period of pyrolysis.

Preferably, airborne dust content is determined in order to reduce false alarms.

Preferably, separate alarm output is provided for any one of, or any combination of, the alarm conditions noted above.

Preferably, in determining the particle size(s) and/or range(s), a first light source for detecting relatively small particle size(s) and/or range(s) and a second light source for detecting relatively large particle size(s) and/or range(s) is used.

Preferably, in determining particle size(s) and/or range(s), the first and second light source are alternatively active.

Preferably, in determining the particle size(s) and/or range(s), a relatively short wavelength of light and a relatively long wavelength of light is used.

According to a further specific aspect of the present invention said pulses of differing wavelength light may be of relatively short wavelength such as violet or blue light and of relatively long wavelength such as red or infrared light.

According to a further specific aspect of the invention, the light source is generated by a light emitting diode (LED) having differing wavelength (colors) and/or utilizing a polarizing filter each filter set to a different relative polarization.

According to a further specific aspect of the invention, the light source is generated by a laser diode having differing wavelength (colors) and/or set to a different relative polarization.

There is also provided according to the invention in a smoke detector system including at least one smoke detector the improvement including sampling of fluid from within a duct and transmitted to at least one detector as described above.

There is also provided according to the invention in a structure having ducting the improvement wherein fluid is sampled for the detection of a pre-determined condition from the duct.

In one specific aspect of the invention sample air from the duct is drawn through a probe mounted within the duct containing an inlet and outlet port.

In a sixth aspect of the invention the sample air may be drawn directly from the duct or tube into the smoke detector device wherein the duct or tube is formed with a venturi construction to generate sufficient relative pressure between the detector chamber and the duct.

In essence, one aspect of the present invention comes about having realized that more than one wavelength of light is required to detect a more complete range of particle sizes and types of fire, and to discriminate among them. Another aspect of the present invention has importantly found that determining particle concentration, size and/or range(s) over a period of time can give a very good indication of whether an alarm condition has been met or is warranted. Yet another aspect of the present invention stems from having at least two sources of light illuminating a particle detection zone and a detection means providing an output signal indicative of a predetermined condition of the particle detection zone. Having two sources of light enables particle size discrimination to be achieved while using no more than one receiving sensor. Yet a further aspect of the present invention is the recognition of dust particles for the monitoring of dust levels or for the avoidance of false fire alarms.

DESCRIPTION OF THE DRAWINGS

FIGS. 11a and 11b show side views of an alternative high volume probe;

FIG. 12a shows a section view of an alternative probe, with the detector body attachment removed;

FIG. 12f shows a high volume detector body attachment;

FIG. 12k shows a low volume detector body attachment;

FIGS. 12b–12e and 12g–12j show various views of the probe of FIG. 12a; and

FIGS. 13a and 13b show side views of an alternative low volume probe.

DESCRIPTION OF PREFERRED EMBODIMENTS

In general terms, the present invention seeks to detect airborne particles and/or to provide discrimination according to particle size using apparatus that has low cost, small size, low weight, high ruggedness, high reliability, low maintenance and long service life, and is suitable for high production volumes. This is achieved with the use of only a single sensor, together with at least two inexpensive light sources. Use of a single sensor and its associated electronic amplifier necessarily designed for high sensitivity with low noise, simplifies the design and reduces the cost of the system. It also avoids any lack of consistency that could occur in the sensitivity and linearity of additional sensors and it avoids the possibility of the incremental addition of noise contributions from plural sensors.

Discrimination of airborne particle size could be achieved in a number of ways. The two or more light sources may differ in wavelength, polarization, position (specifically the solid angle of incidence to the detection zone axis), or a combination of these.

In the preferred embodiment of the invention, two light emitting diodes (LED's) operating at different wavelengths are employed. This permits the use of wavelengths as distant as 430 nm (blue) and 880 nm (infrared) such that the wavelengths are separated by a full octave. Such a large difference in wavelength can produce a significantly different strength of signal when light of alternate wavelength is scattered off particles toward the sensor. Alternative combinations such as 430 nm (blue) with 660 nm (red) are possible. Closer-spaced wavelengths such as 525 nm (green)

with 660 nm (red) could be used, accompanied by a reduction in size discrimination and sensitivity to small particles.

It is known from Rayleigh theory that the intensity of the scattered light reduces according to the fourth power of wavelength, for particles smaller than the wavelength of light. This has proven relevant to smoke detection in experiments using Xenon lamps which produce a complete spectrum embracing infrared, visible and ultraviolet wavelengths, where it was found that wavelengths in the blue region are necessary for the detection of certain kinds of fires liberating small particles.

Therefore, a particular advantage of being able to employ a blue light source is that its short wavelength provides high resolution of small particles that become invisible at longer wavelengths. Whereas a blue or violet laser diode may be preferable to a blue LED, the former are expensive, have increased alignment complexity, require automatic power control and have a lower tolerance of elevated temperatures. The combination of readily available red and infrared laser diodes could be used, but in addition to the difficulties presented by using lasers, these longer wavelengths fail to adequately resolve small particles.

Accordingly the preferred embodiment of the invention is configured to utilize the broad beam spread of a high-intensity LED (approx 12 deg). Although the broad spread of the LED beam could be confined by focusing with a lens, this adds cost, complexity in alignment and size to the product. Whereas the LED does not have the localized high light intensity of a collimated laser beam, the aggregate intensity of the LED light scattered from the large volume of the detection zone when integrated on the sensor is of comparable magnitude. Therefore the sensitivity of the LED based system is comparable with laser, but the cost is reduced without compromising reliability.

Nevertheless, the same invention could be configured to use laser diodes as alternative light sources of differing wavelength, polarization or position (angle). Such arrangements can provide particle size discrimination also, but at a higher cost and greater temperature intolerance than LED designs.

The ability to use LED's is achieved by the novel configuration of the optical chamber which accommodates the broad projector beam angle of each LED, opposite a specially designed light trap located beyond the detection zone, to completely absorb the remnant projected light, thereby preventing its detection at the sensor. The chamber also contains a further light trap opposite the sensor and beyond the detection zone, to eliminate stray projected light from being detected. Thus the signal-to-noise ratio caused by remnant projected light compared with the detected scattered light, is maximized to ensure very high sensitivity of the system. This is further ensured by the close mutual proximity of the LED's and the sensor to the detection zone, so that inverse-square light intensity losses are minimized. Moreover, a lens is preferably used in conjunction with the sensor to gather scattered light from throughout the detection zone while minimizing visibility of chamber wall surfaces as a result of focusing. Control irises are used to further minimize stray light reaching the sensor. Through the combination of all these methods the system sensitivity is on the order of 0.01 to 0.1%/m equivalent smoke obscuration.

It should be noted that the ability to utilize a broad projector beam enables the use of laser diodes without costly collimation optics.

In one preferred embodiment of the invention, each light source is pulsed in sequence for a short period such as 10 mS. At the sensor, a signal is generated in response to each pulse of scattered light at each wavelength. The system is pre-calibrated to account for the sensitivity of the sensor at each wavelength, preferably by adjusting the intensity of the LED projections during manufacture. The signals are amplified using digital filtering to improve the signal-to noise ratio, and both the absolute and relative amplitudes of the pulse signals are stored. The absolute value indicates the particle concentration whereas the relative value indicates the particle size or the average size of a group of particles. From Rayleigh theory, at a given mass concentration of airborne particles, the long wavelength light will produce a low amplitude signal in the case of small particles, or a large amplitude signal in the case of large particles. The short wavelength light will produce a relatively equal amplitude signal in the case of both small and large particles. By comparing the ratio of the signals it is therefore possible to determine whether the particles are large or small.

Signals produced over a period of time are analyzed according to trend. A slow increase in the concentration of large particles is indicative of pyrolysis and eventually a smoldering condition. Alternatively, a rapid increase in small particles is indicative of a fast flaming fire and, in the absence of a prior period of pyrolysis and smoldering, could indicate the involvement of accelerants (such as with arson). This information is used to produce separate alarm outputs in the case of smoldering and flaming fires, or alternatively, to reduce the alarm activation threshold (i.e., provide earlier warning) in the case of flaming fires (which are more dangerous).

It should be noted that the concentration of smoke alone, does not necessarily indicate the level of danger of an incipient fire. The concentration detected will depend upon the degree of smoke dilution by fresh air, and the proximity of the incipient fire to the detector. By characterizing the smoke in accordance with our invention it becomes possible to determine the level of smoke concentration necessary for an alarm, that is appropriate to the protected environment, thereby providing early warning with minimum false alarms. Moreover, the low cost of the system encourages its comprehensive use throughout a facility.

In a further embodiment of the invention, particle size discrimination is used to determine the airborne dust content for the purpose of avoiding false alarms or for dust level monitoring within the protected environment. Two LED's may be used, but by the use of additional LED's it is possible to discriminate within differing particle size ranges.

Preferred embodiments of the present invention will now be described with reference to the accompanying drawings.

Figure 1A:
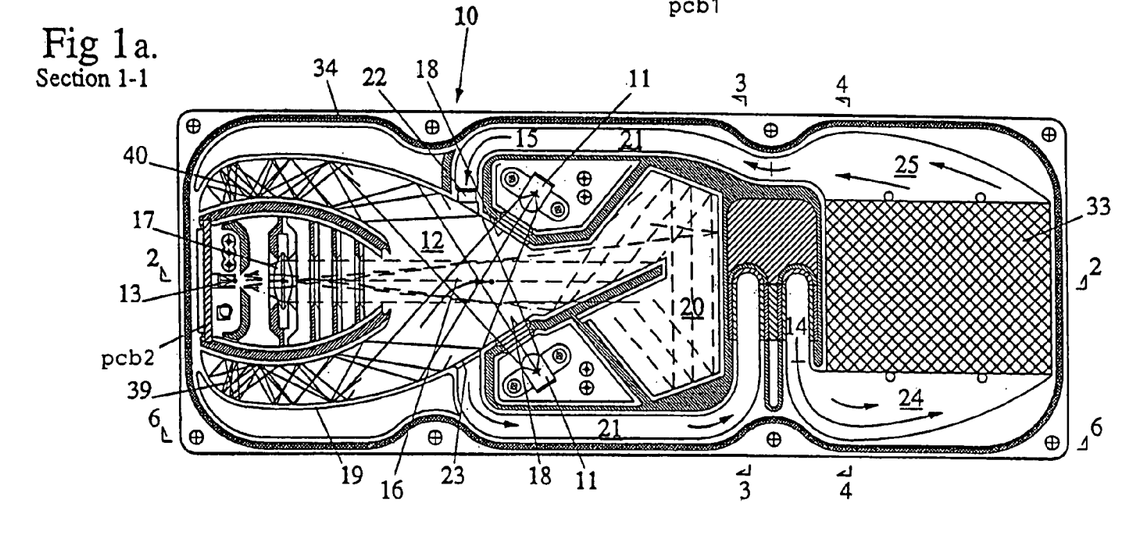
FIG. 1a is a sectional plan view taken on line 1—1 of a smoke detector body.
Figures 1B, 3, 4:
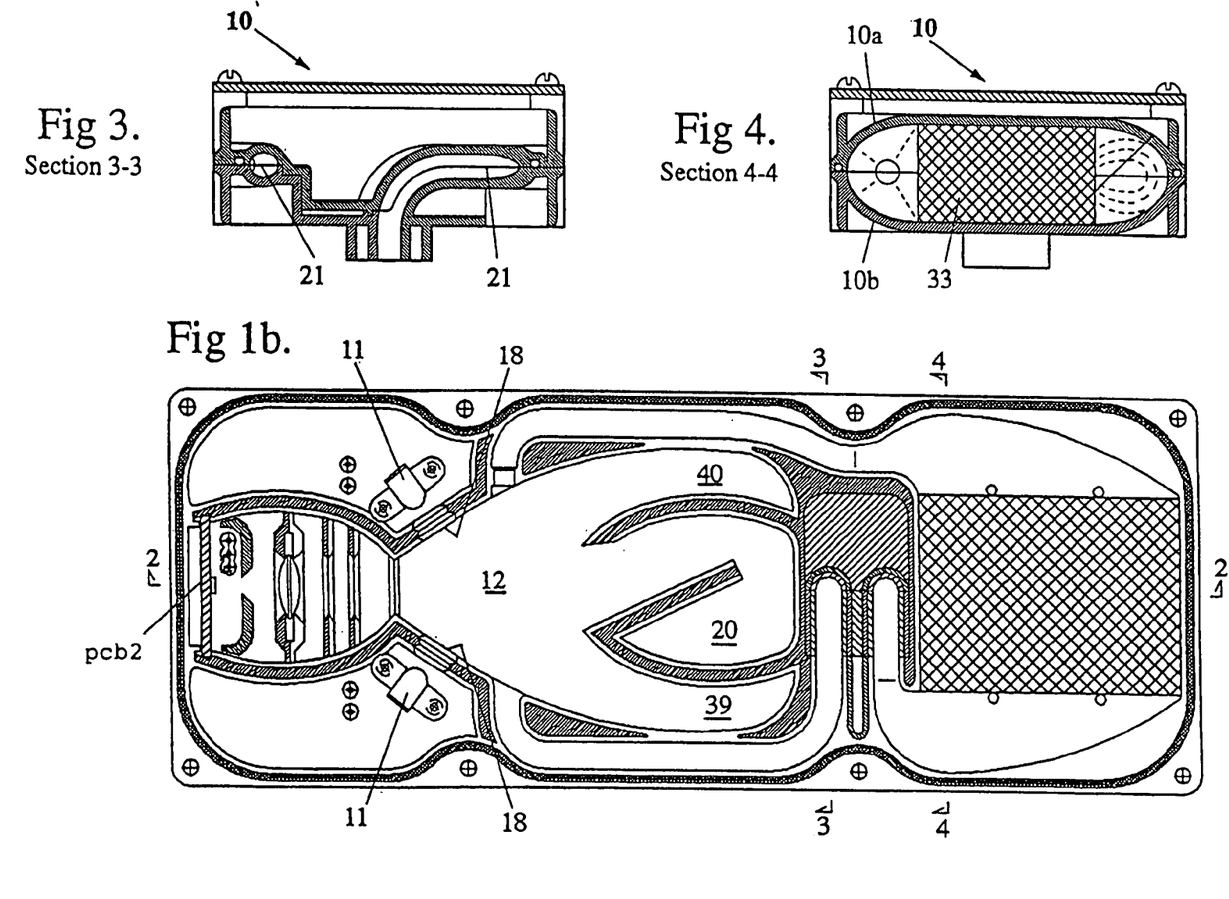
FIG. 1b illustrates in plan view, an alternative smoke detector body.
FIG. 3 is a cross-sectional view taken on line 3—3 of a smoke detector body showing the gas sample inlet pipework.
FIG. 4 is a cross-sectional view taken on line 4—4 of a smoke detector body showing its filter chamber and diffuser ducting.

In one embodiment of the invention, and referring to FIG. 1, the smoke detector housing 10 is produced by the molding of two substantially identical halves 10a, 10b (see FIG. 4). Two LED lamps 11 are positioned to project light across the detection chamber 12 into a region that is viewed by the sensor 13. Smoke 14 is drawn across the chamber 12 in the direction of arrows 15 so that it can be irradiated by the projectors 11 in sequence. Some light 16 scattered off the airborne smoke particles is captured by a focusing lens 17 onto the receiving sensor 13.

A series of optical irises 18 confine the spread of the projector beams and another series of irises 19 confine the field of view of the sensor 13. An absorber gallery 39/40 (light trap) is provided opposite each projector 11 to absorb essentially all of the remaining essentially unscattered light and thereby prevent any swamping of the scattered light 16 at the sensor 13 by the projected light. A further light trap 20 is provided opposite the sensor to further ensure that essentially no projector light is able to impinge on the sensor.

The smoke detector housing 10 preferably incorporates pipework 21 to provide airflow through the detector chamber 12. This pipework 21 may incorporate a nozzle 22 opposite a collector 23, to direct the airflow across the chamber 12, such that the chamber is quickly purged of smoke in the event that the smoke level is reducing. Included in the pipework pathway is a dust filter 33. Coupling to the dust filter cavity is by inlet and outlet diffusers 24, 25 designed to minimize head loss (pressure drop) in the airflow through the detector, and to facilitate the use of a large filter 33 for long service life. Over a period of years, a small quantity of fine dust may pass through the filter. To prevent or minimize soiling, the arrangement of the nozzle and collector is such as to minimize deposition of dust on the chamber walls and optical surfaces.

Figure 1C:
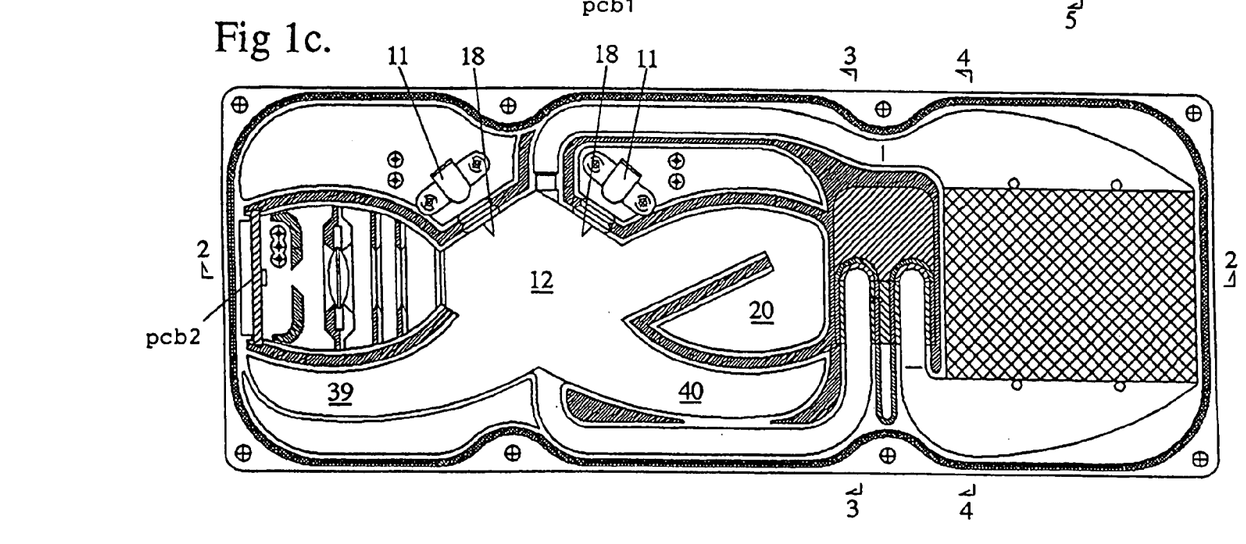
FIG. 1c illustrates in plan view, a further alternative smoke detector body.

FIGS. 1b and 1c illustrate alternative positioning of the light source(s) 11 of FIG. 1a. This has necessitated the re-positioning of the light trap 39, 40. In many other respects, the features of FIGS. 1b and 1c are identical to the illustration of FIG. 1 and the accompanying description. FIGS. 1b and 1c do not show all the detail of FIG. 1a, only as a matter of clarity. It is to be noted that FIGS. 1b and 1c allow for backscatter detection or a combination of back and forward scatter, i.e., different angles.

Figure 2:
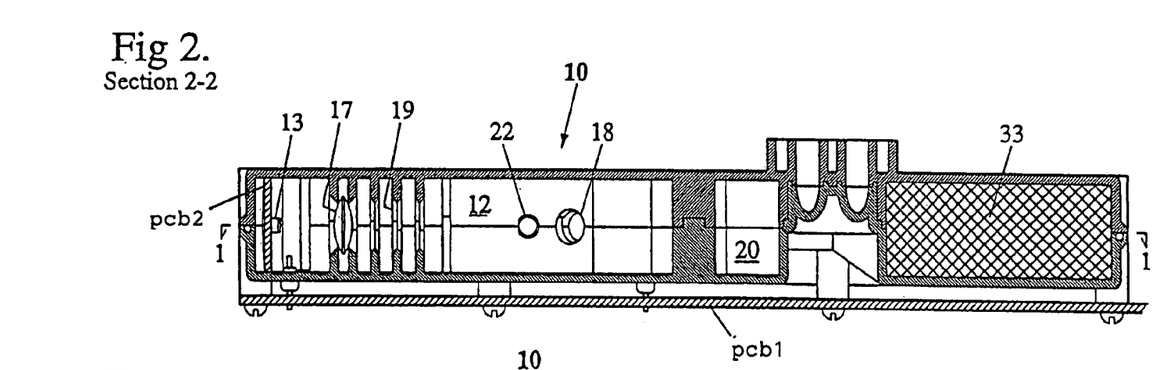
FIG. 2 is a sectional elevational view taken on line 2—2 of the smoke detector body.

FIG. 2 illustrates a sectional elevation view taken along line 2—2 of the smoke detector body of FIG. 1. Again, many features shown in FIG. 1a are numbered identically. FIG. 2 indicates the preferred position of the main electronics printed circuit board PCB1 for efficient and low-interference electrical connection to the projecting light sources and the receiving sensor including its pre-amplifier printed circuit board PCB2. Conveniently the upper half of the smoke detector body 10b may be removed without disturbing the connections to PCB1 for the purposes of setup and maintenance.

Referring to FIG. 3, there is shown a cross-sectional view taken along line 3—3 of FIG. 1 and showing the gas sample inlet pipework including socket and bends.

A cross-sectional view taken on line 4—4 of FIG. 1 shows its filter chamber and is represented in FIG. 4. The filter element is preferably of open-cell foam construction with a relatively large filter pore size such as 0.1 mm. This causes dust particles to be arrested progressively throughout the large depth of the element. Use of such a large pore size means that smoke particles are not arrested in the filter, even when the filter becomes loaded with dust, which if it occurred would reduce the sensitivity of the detector to smoke. This element is easily removed for cleaning or renewal.

Figures 5, 7, 8, 8A, 8B, 8C:
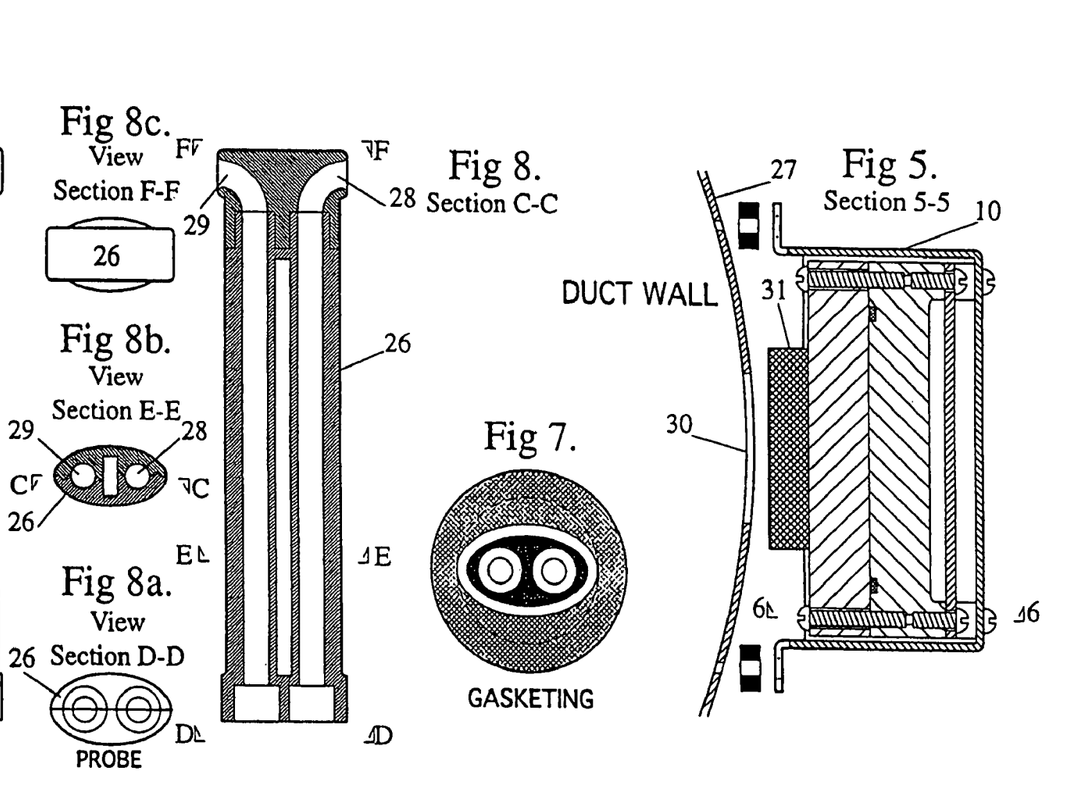
FIG. 5 is a sectional view taken on line 5—5 of the smoke detector body and housing.
FIG. 7 is an end view of the inlet/outlet gas port to the smoke detector body with gasketing.
FIG. 8 is a sectional side view of duct probe taken on a line C—C.
FIG. 8a is an end view of the probe that attaches to the smoke detector body.
FIG. 8b is a cross-sectional view of the probe taken on a line E—E.
FIG. 8c is an end view of the probe remote from the detector body.
Figure 6:
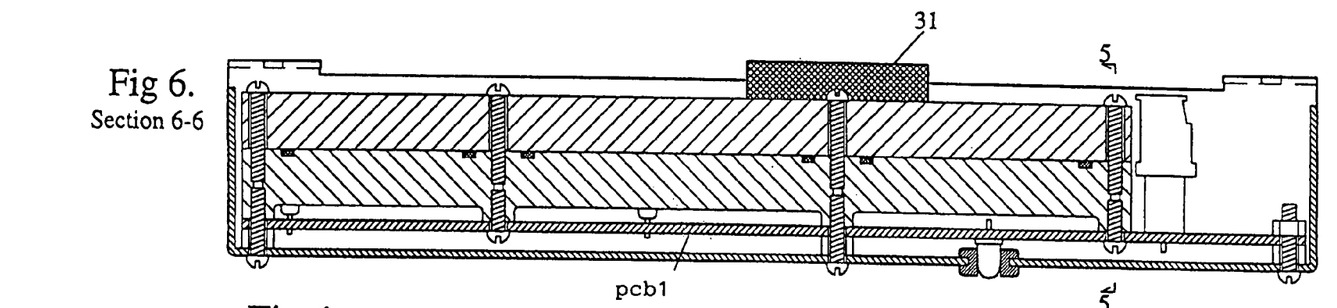
FIG. 6 is a sectional view taken on line 6—6 of the smoke detector body and housing.

In FIG. 5, there is a sectional view taken long line 5—5 of the smoke detector body of FIG. 6. This indicates how the detector body and the detector housing are secured with screws, and in exploded view shows where the housing may be attached to the duct such as a circular ventilation duct (which is more challenging than a flat-sided duct). For example, attachment may be achieved by screws, magnets or adhesive tape.

FIG. 6 illustrates a sectional view taken on line 6—6 of FIG. 5 of the smoke detector body. FIG. 1a also shows line 6—6. In FIG. 6 a view of the outer casing, mounted on a pcb PCB1, together with a gasket 31 is shown. This particular arrangement is suitable for mounting a duct, although the present invention should not be limited to only such an application.

FIG. 7 is an end view of the inlet/outlet gas port to the smoke detector body showing gasket 31 in plan view. This gasket provides a releasable seal to a duct such as a round ventilation duct of unspecified radius The following description relates to one preferred arrangement of the invention, and with reference to FIGS. 8, 8a, 8b, 8c and 9. It is to be noted that the following description equally applies to the alternative high volume and low volume embodiments shown in FIGS. 11a, 11b, 12a to 12k, and 13a and 13b. The same numeral references have been used in the various figures to avoid duplication. The high volume embodiment is used when fluid flow in the duct is relatively high. Thus the inlet and outlet openings 28 and 29, respectively are designed to be smaller, so with a high volume of fluid flow, a smaller sample area is captured and substantially the same volume of fluid to the detector of the present invention. Equally, the low volume embodiment is designed with relatively larger openings 28 and 29, as the fluid flow is lower, a larger opening is provided to present substantially the same amount of fluid flow to the detector of the present invention.

Figure 11A:
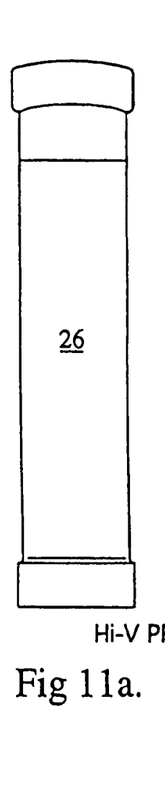
Figures 11B, 12B, 12C, 12D, 12E, 12F:
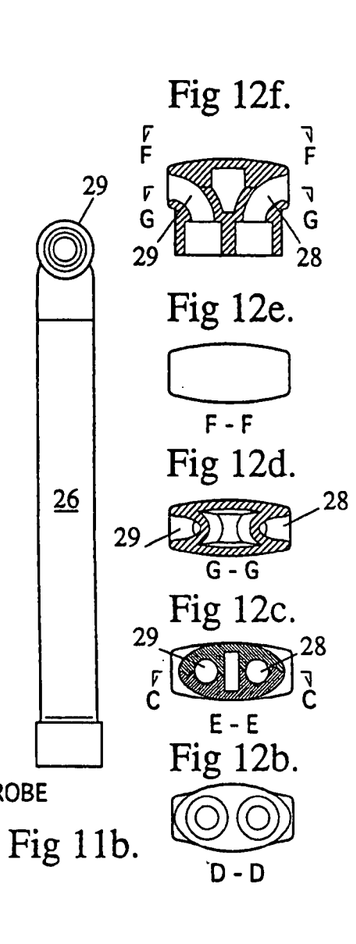
Figures 12A, 12G, 12H, 12I, 12J, 12K, 13A:
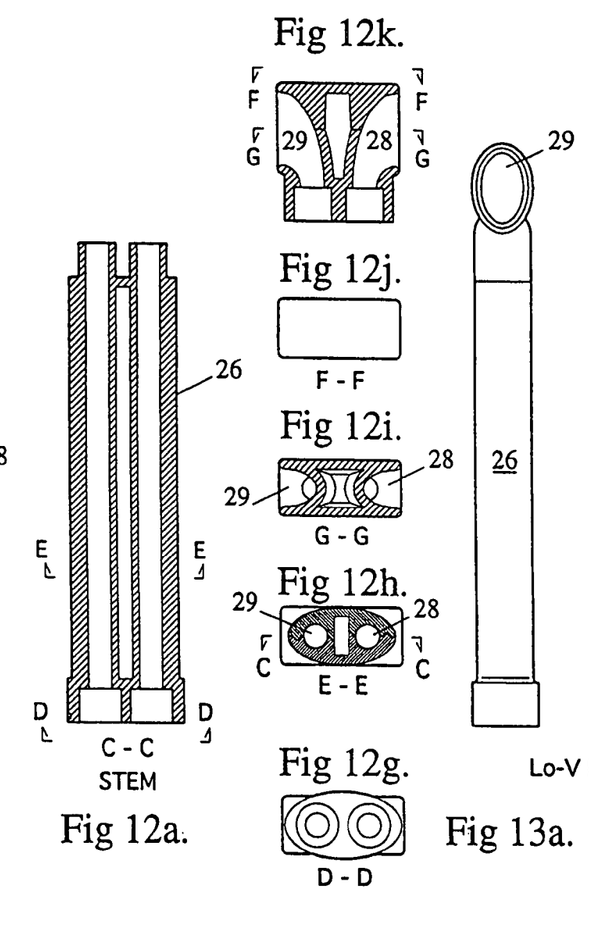
Figure 13B:
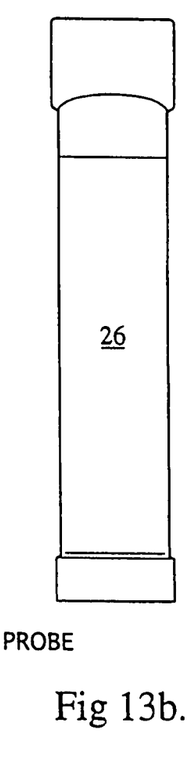

The pipework is configured with appropriate bends and sockets suitable for attachment to a probe 26, which draws smoke from the ventilation duct 27. The probe 26 is preferably of unit construction containing an inlet port 28 and an outlet port 29, so that only one penetration hole 30 need be cut into the duct wall to provide access for the probe 26. This hole is releasably sealed using a closed-cell foam gasket 31 to prevent leakage. FIG. 8 shows a view along line C—C from FIG. 8b. FIG. 12a also shows a view along line C—C of FIGS. 12c and 12h. FIG. 8a shows a view along line D—D of FIG. 8. FIG. 12b shows a view along line D—D of FIG. 12a for the high volume embodiment. FIG. 12g shows a view along line D—D of FIG. 12a for the low volume embodiment. FIG. 8b shows a sectional view along line E—E of FIG. 8 indicating that it comprises a stem with a detachable head. FIGS. 12c and 12h show, respectively, high volume and low volume embodiments of the probe viewed along line E—E of FIG. 12a. FIG. 8c shows a view along line F—F. FIGS. 12e and 12j show plan views of the, respective, high volume and low volume probes. FIGS. 12d and 12l show sectional views of the heads of the, respective high and low volume probes.

The probe 26 is suitable for being inserted into a duct by requiring only a single round penetration of the duct. The probe is inserted so that its inlet faces upstream and its outlet faces downstream. The probe is designed to provide an adequate airflow rate through the detection chamber 12, driven by the dynamic head associated with the airflow in the ventilation duct 27. This dynamic head produces a pressure drop across the inlet port 28 and outlet port 29 of the probe 26, sufficient to overcome the combined restriction of the detection chamber 12, pipework 21 and dust filter 33. The efficiency of the probe is maximized by the use of rounding of the inlet orifice followed by a bend to change the direction of the sampled flow with minimum loss. This is repeated at the outlet. The inlet and outlet bends are incorporated without any requirement to enlarge the duct penetration. This high efficiency enables the use of an effective dust filter to ensure a long service interval for the product, such as 10 years in a typical office environment. Given such a long interval, it is considered appropriate (but not essential) that the detector body 10 can be easily dismantled for cleaning and re-calibration, avoiding the need for a removable filter cartridge that is costly and difficult to make airtight. The high efficiency of the probe also facilitates its use in ventilation ducts operating at relatively low air velocity such as 4 m/sec. For use at low ventilation duct velocities, an alternative probe head is provided. This uses an enlarged air scoop design which incorporates a diffuser to efficiently accelerate the inlet air and ensure that the detector's rapid response to smoke is maintained.

Figure 9:
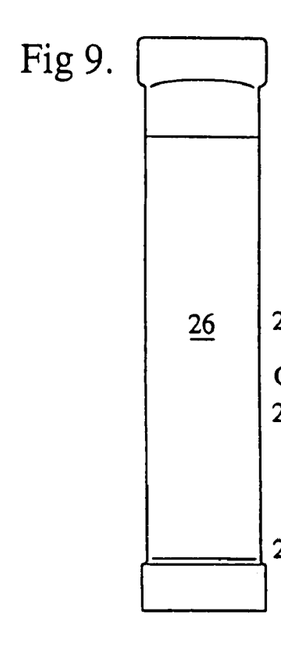
FIG. 9 is a side elevational view of the duct sampling probe.

In a preferred embodiment of the invention, with reference to FIGS. 8b and 9, the probe 26 is constructed with an elliptical or similar cross-section that will minimize drag (to minimize restriction to flow in the ventilation duct), as well as minimizing forced vibration at the Strouhal frequency caused by the duct flow. In the particular embodiment illustrated by FIGS. 8b and 9, the aerodynamic coefficient of drag is reduced by a factor of ten compared with a pair of round pipes of similar dimensions. FIGS. 12b to 12k show similar features, but in respect of the high and low volume probes. The advantages of using an elliptical shape instead of an aerofoil are that the probe may be installed in either direction, and that the overall width of the probe is reduced, without unduly compromising the reduction in drag. By the addition of further stem sections, the probe 26 may be extended in length to meet the needs of different sized ductwork, ensuring adequate flow without the need of an aspirator. The pressure inside the duct 27 can be significantly different from the ambient atmosphere outside the duct (where the detector is usually mounted). In a preferred embodiment of the invention best shown in FIGS. 1 and 6, the halves of the chamber are releasably joined in an airtight manner by means of only one continuous O-ring seal 34. This sets the detector chamber internal pressure to approximate that of the ventilation duct and avoids any leakage to or from ambient atmosphere.

Leakage into the detector could cause an unwanted alarm from smoke in the ambient environment. Leakage of smoke from the detector to the ambient environment could cause an unwanted alarm in other smoke detection equipment protecting that environment.

Figure 10:
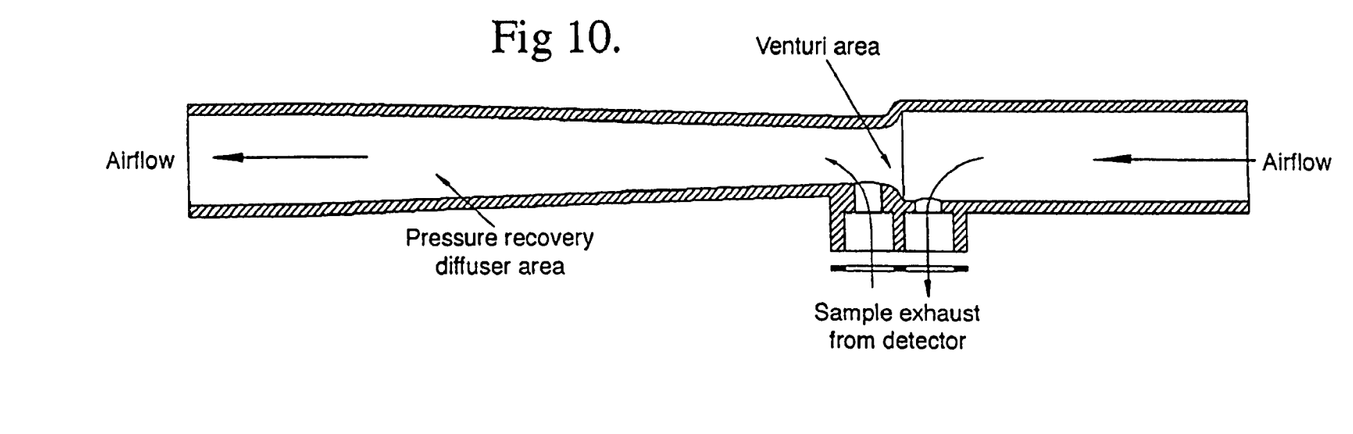
FIG. 10 is a sectional view of an alternate duct or pipe sampling configuration.

Alternatively, with reference to FIG. 10 if a relatively small duct or pipe is used such that the probe in inappropriate, then this duct may be configured to produce a venturi which develops the necessary pressure drop to ensure an adequate flow rate through the detector chamber, filter and pipework. Again only a small proportion of the smoke need be passed through the detector and this proportion is minimized in order to minimize the rate of detector soiling and filter loading, thereby to maximize the service interval.

The invention claimed is:

1. A device for detection of particles suspended in a fluid, the device comprising light source(s) adapted to provide at least a first polarized illumination and a second polarized illumination, a particle detection zone through which a stream of sample fluid is adapted to flow, logic means adapted to alternately illuminate the detection zone with either the first or second illumination, sensor for reception of light scattered off particles within the detection zone and output means to provide an indication of a predetermined condition in the detection zone, wherein a majority of light received by the sensor is the light scattered off particles within the detection zone.

2. The device as claimed in claim 1, wherein at least one of the polarized first and second illuminations is provided by light from the light sources(s) being projected through polarizing filters, each with a different relative polarization.

3. The device as claimed in claim 1 wherein at least one of the polarized first and second illuminations is provided by a source of light having different polarization.

4. The device as claimed in claim 3, wherein the source of light having different polarization is a laser diode set to a different polarization and/or wavelength.

5. The particle detection device as claim in claim 1, wherein the light sources(s) comprises at least two light sources, the light sources(s), the particle detection zone, the logic means, the sensor and the output means are mechanically fixed in position, the first and second illuminations are independently radiated, the first and second illuminations are of different polarization, the first and second illuminations are provided from different positions, and/or the first and second illuminations are of different wavelength, one of short wavelength light and the other of long wavelength light.

6. A smoke detector comprising the particle detection device as claimed in claim 1.

7. A probe adapted to be installed in a conduit, such as a duct through which a fluid may flow, the probe being adapted to communicate fluidly with a device, detector or detection unit as claimed in claim 1, the probe comprising
a first portion adapted to be inserted into the conduit,
the first portion having an inlet for receiving an upstream fluid flow, and an outlet portion having an outlet for outputting a downstream flow,
the inlet and outlet portions each having a channel which is curved to enable a change of direction of the fluid flow within the probe while substantially minimizing flow resistance.

8. A device for detection of particles suspended in a fluid, the device comprising a body portion, light source(s) adapted to provide at least a first illumination and a second illumination, a particle detection zone through which a stream of sample fluid is adapted to flow, logic means adapted to alternately illuminate the detection zone with either the first or second illumination, sensor for reception of light scattered off particles within the detection zone and output means to provide an indication of a predetermined condition in the detection zone, wherein
the body portion is configured from two substantially similar halves, and a majority of light received by the sensor is the light scattered off particles within the detection zone.

9. The device as claimed in claim 8, wherein the first and second illuminations are disposed substantially opposite to an area of particle detection.

10. The device as claimed in claim 9, wherein the body portion is configured substantially axially similar.

11. A smoke detector comprising the particle detection device as claimed in claim 8.

12. A particle detector having a body, at least two light projectors mounted within the body for projecting light into a detection zone adapted to receive an air sample, at least one light receiving sensor mounted in the body to receive scattered light from the detection zone, the light projectors being adapted to project light into the detection zone, wherein the projected light includes pulses of differing wavelength, polarization and/or angle impinging upon smoke and dust particles entering the detection zone and creating scattered light indicative of a range of smoke particle sizes and/or the existence of dust particles, said sensor upon receiving at least some of said scattered light being adapted to provide a signal which upon analysis enables the determination of particle concentration and particle size and/or range, wherein a majority of light received by the sensor is scattered light created by the projected light impinging upon smoke and dust particles entering the detection zone.

13. A smoke detector comprising the particle detector as claimed in claim 12.

14. The device as claimed in claim 1, wherein dust particles entering the detection zone scatter light indicative of one of a range of smoke particle sizes, the existence of dust particles, and a range of smoke particle sizes and the existence of dust particles, said sensor means upon receiving at least some of said scattered light providing a signal enabling the determination of particle concentration and particle size and/or range.

15. The device as claimed in claim 8, wherein dust particles entering the detection zone scatter light indicative of one of a range of smoke particle sizes, the existence of dust particles, and a range of smoke particle sizes and the existence of dust particles, said sensor means upon receiving at least some of said scattered light providing a signal enabling the determination of particle concentration and particle size and/or range.

16. A device for detecting particles comprising:
at least two light sources for projecting light of differing wavelength, polarization and/or angle; and
at least one sensor for receiving scattered light, wherein the scattered light is produced by the projected light impinging upon particles, said sensor providing a signal representing at least one of particle concentration, particle size and particle range, wherein a majority of light received by the sensor is the scattered light produced by the projected light impinging upon the particles.

17. A method of detecting particles comprising:
projecting light of differing wavelength, polarization and/or angle from at least two light sources;
receiving scattered light produced by the projected light from the at least two light sources impinging upon particles by at least one sensor, wherein a majority of light received by the sensor is the scattered light produced by the projected light from the at least two light sources impinging upon particles; and
generating a signal representing at least one of particle concentration, particle size and particle range based on the received scattered light.

18. The device as claimed in claim 1, wherein substantially all of the light received by the sensor is the light scattered off particles within the detection zone.

19. The device as claimed in claim 8, wherein substantially all of the light received by the sensor is the light scattered off particles within the detection zone.

20. The particle detector as claimed in claim 12, wherein substantially all of the light received by the sensor is scattered light created by the projected light impinging upon smoke and dust particles entering the detection zone.

21. The device as claimed in claim 16, wherein substantially all of the light received by the sensor is the scattered light produced by the projected light impinging upon the particles.

22. The method as claimed in claim 17, wherein substantially all of the light received by the sensor is the scattered light produced by the projected light from the at least two light sources impinging upon particles.

* * * * *